US012803051B2

(12) United States Patent
Nam et al.

(10) Patent No.: US 12,803,051 B2
(45) Date of Patent: Nov. 17, 2026

(54) ELECTROLYTE SOLUTION FOR LITHIUM SECONDARY BATTERY AND LITHIUM SECONDARY BATTERY COMPRISING THE SAME

(71) Applicants: Hyundai Motor Company, Seoul (KR); Kia Corporation, Seoul (KR); UNIST (Ulsan National Insitute of Science and Technology), Ulsan (KR)

(72) Inventors: Hui Beom Nam, Hwaseong (KR); Jun Ki Rhee, Suwon (KR); Ko Eun Kim, Cheongju (KR); Sung Ho Ban, Hwaseong (KR); Yoon Sung Lee, Suwon (KR); Dong Uk Kim, Ulsan (KR); Seung Min Lee, Ulsan (KR); Min Pyeong Kim, Ulsan (KR); Hyeong Jun Kim, Ulsan (KR); Sang Kyu Kwak, Ulsan (KR); Sung You Hong, Ulsan (KR)

(73) Assignees: Hyundai Motor Company, Seoul (KR); Kia Corporation, Seoul (KR); UNIST (Ulsan National Insitute of Science and Technology), Ulsan (KR)

( * ) Notice: Subject to any disclaimer, the term of this patent is extended or adjusted under 35 U.S.C. 154(b) by 648 days.

(21) Appl. No.: 18/360,049

(22) Filed: Jul. 27, 2023

(65) Prior Publication Data

US 2024/0162491 A1 May 16, 2024

(30) Foreign Application Priority Data

Nov. 1, 2022 (KR) ........................ 10-2022-0143829

(51) Int. Cl.

| | |
|---|---|
| ***H01M 10/0567*** | (2010.01) |
| ***C07D 249/08*** | (2006.01) |
| ***H01M 4/36*** | (2006.01) |
| ***H01M 4/505*** | (2010.01) |
| ***H01M 4/525*** | (2010.01) |
| ***H01M 4/587*** | (2010.01) |
| ***H01M 10/0525*** | (2010.01) |
| ***H01M 10/0568*** | (2010.01) |
| ***H01M 10/0569*** | (2010.01) |
| ***H01M 10/42*** | (2006.01) |
| *H01M 4/02* | (2006.01) |

(52) U.S. Cl.

CPC ...... *H01M 10/0567* (2013.01); *C07D 249/08* (2013.01); *H01M 4/364* (2013.01); *H01M 4/505* (2013.01); *H01M 4/525* (2013.01); *H01M 4/587* (2013.01); *H01M 10/0525* (2013.01); *H01M 10/0568* (2013.01); *H01M 10/0569* (2013.01); *H01M 10/4235* (2013.01); *H01M 2004/027* (2013.01); *H01M 2004/028* (2013.01); *H01M 2220/20* (2013.01); *H01M 2300/004* (2013.01)

(58) Field of Classification Search

CPC .. H01M 10/0567; H01M 4/364; H01M 4/505; H01M 4/525; H01M 4/587; H01M 10/0525; H01M 10/0568; H01M 10/0569; H01M 10/4235; H01M 2004/027; H01M 2004/028; H01M 2220/20; H01M 2300/004; C07D 249/08

See application file for complete search history.

(56) References Cited

U.S. PATENT DOCUMENTS

| | | | | |
|---|---|---|---|---|
| 2013/0298386 A1* | 11/2013 | Tarascon ........... | H01M 10/0525 29/623.1 |
| 2016/0268636 A1* | 9/2016 | Cha ..................... | H01M 10/052 |
| 2021/0043977 A1 | 2/2021 | Jang et al. | |

FOREIGN PATENT DOCUMENTS

| | | | |
|---|---|---|---|
| JP | 2014-518001 | A | 7/2014 |
| KR | 10-2019-0092149 | A | 8/2019 |
| KR | 10-2020-0048511 | A | 5/2020 |
| KR | 10-2207522 | B1 | 1/2021 |
| WO | 2012/161989 | A1 | 11/2012 |

OTHER PUBLICATIONS

Bai et all , Journal of Organic Chemistry (2022), 87(7), 4998-5004 (Year: 2022).*

K. Kim et al., "Electrolyte-Additive-Driven Interfacial Engineering for High-Capacity Electrodes in Lithium-Ion Batteries: Promise and challenges", ACS Energy Letters, vol. 5, pp. 1537-1553 (2020).

W. Li et al., "High-voltage positive electrode materials for lithium-ion batteries", Chem. Soc. Rev., vol. 46, pp. 3006-3059 (2017).

* cited by examiner

*Primary Examiner* — Alexander Usyatinsky

(74) *Attorney, Agent, or Firm* — Fox Rothschild LLP

(57) ABSTRACT

Disclosed are an electrolyte solution for a lithium secondary battery capable of improving the output and lifespan characteristics at high temperature of a lithium secondary battery, and a lithium secondary battery including the same. An electrolyte solution for a lithium secondary battery includes a lithium salt, a solvent, and a functional additive, and in particular, the functional additive includes (4-(1H-1,2,4-triazol-1-yl)phenyl)(fluorosulfonyl)sulfamoyl fluoride.

17 Claims, 3 Drawing Sheets

ELECTROLYTE SOLUTION FOR LITHIUM SECONDARY BATTERY AND LITHIUM SECONDARY BATTERY COMPRISING THE SAME

CROSS REFERENCE TO RELATED APPLICATION

The present application claims priority to Korean Patent Application No. 10-2022-0143829, filed Nov. 1, 2022, the entire contents of which is incorporated herein for all purposes by this reference.

TECHNICAL FIELD

The present disclosure relates to an electrolyte solution for a lithium secondary battery and a lithium secondary battery including the same. The electrolyte solution for a lithium secondary battery can improve output and lifespan characteristics at high temperature of a lithium secondary battery.

BACKGROUND

A lithium secondary battery is an energy storage system including a positive electrode providing lithium and a negative electrode receiving the lithium during charging, an electrolyte serving as a lithium ion transfer medium, and a separator separating the positive electrode and the negative electrode from each other. The lithium secondary battery generates and stores an electric energy through a change of chemical potentials when intercalation/deintercalation of lithium ions is performed at the negative and positive electrodes.

The lithium secondary battery has mainly been used in a portable electronic device, but recently, with the commercialization of an electric vehicle (EV) and a hybrid electric vehicle (HEV), the lithium secondary battery has also been used as an energy storage means of the electric vehicle and the hybrid electric vehicle.

In particular, as a next-generation energy source for green growth, the demand for secondary batteries has been increasing.

The lithium secondary battery includes four core materials, a positive electrode, a negative electrode, a separator, and an electrolyte, and the performance of the lithium secondary battery is greatly affected by the characteristics of these core materials.

Meanwhile, in order to increase a driving distance of the electric vehicle, researches to increase an energy density of the lithium secondary battery have been made, and the energy density of the lithium secondary battery can be increased through high capacity of the positive electrode.

The high capacity of the positive electrode may be achieved through Ni-rich that is a method for increasing Ni contents of Ni—Co—Mn based oxide forming a positive-electrode active material, or may be achieved through voltage heightening of a positive-electrode charging voltage.

However, since the Ni—Co—Mn based oxide in the Ni-rich state has a high interfacial reactivity and an unstable crystal structure, deterioration during cycle is accelerated, and thus it is difficult to secure a long-lifespan performance.

For example, in the case of the positive electrode made of Ni—Co—Mn-based oxide in the Ni-rich state, due to the high Ni content and the high reactivity of $Ni^{4+}$ formed during charging in the electrolyte solution, there was a problem that reduced the safety and lifespan of the battery, such as the oxidative decomposition of electrolyte solution, the interface reaction of positive electrode-electrolyte solution, metal elution, gas generation, phase change to inert cubic, increased possibility of metal deposition on a negative electrode, increased interfacial resistance of battery, accelerated deterioration, deterioration of charge/discharge performance, and increased instability at high temperature.

In addition, researches on silicon-graphite based negative-electrode active materials containing silicon have been continuously conducted to increase the capacity of the negative electrode in line with the increase in the capacity of the positive electrode. But there was still a problem in that the lifespan was reduced due to the volume change in silicon and interfacial instability.

In other words, in the case of the silicon-graphite based negative-electrode, there was a problem that the lattice volume increased by greater than 300% during charging and the volume decreased during discharging. Also, there was a problem that reduced the safety and lifespan of the battery, such as the formation of large amounts of Si surface inactive chemical species due to the interfacial reaction with $LiPF_6$ salt, low SEI coverage, weak mechanical strength, increased interfacial resistance, performance degradation, gas generation, and electrolyte consumption.

The description given in the related art is only to understand the background of the present disclosure, but should not be recognized as a prior art already known to a person skilled in the art.

SUMMARY

In preferred aspects, provided are, inter alia, an electrolyte solution for a lithium secondary battery capable of improving the output and lifespan characteristics of a lithium secondary battery at high temperature, and a lithium secondary battery including the same.

The technical objects that can be achieved through the present disclosure are not limited to what has been particularly described hereinabove and other technical objects not described herein will be more clearly understood by persons skilled in the art from the following detailed description.

In an aspect, provided is an electrolyte solution for a lithium secondary battery including a lithium salt, a solvent component, and a functional additive. In particular, the functional additive may include a first electrode film additive, which is (4-(1H-1,2,4-triazol-1-yl)phenyl)(fluorosulfonyl)sulfamoyl fluoride, represented by the following Formula 1:

[Formula 1]

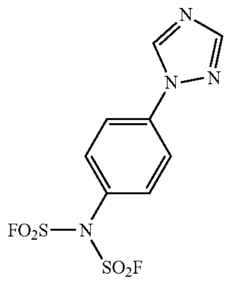

In an aspect, provided is an electrolyte composition for a lithium secondary battery comprising: 1) a lithium salt and 2) benzo[d]thiazol-6-yl(fluorosulfonyl)sulfamoyl fluoride, represented by the following Formula 1:

[Formula 1]

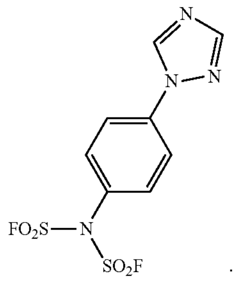

The electrolyte solution or composition may suitably include the first electrode film additive in an amount of about 0.01 to 0.5% by weight based on the total weight of the electrolyte solution.

Preferably, the electrolyte solution may suitably include the first electrode film additive in an amount of about 0.01 to 0.3% by weight based on the total weight of the electrolyte solution.

The functional additive may further include a negative-electrode film additive which is vinylene carbonate (VC).

Preferably, the electrolyte solution may suitably include the negative-electrode film additive in an amount of about 0.5 to 2.0% by weight based on the total weight of the electrolyte solution.

The functional additive may further include a second electrode film additive which is lithium difluorophosphate ($LiPO_2F_2$).

Preferably, the electrolyte solution may suitably include the second electrode film additive in an amount of about 0.5 to 2.0% by weight based on the total weight of the electrolyte solution.

The lithium salt may suitably include one or more selected from the group consisting of $LiPF_6$, $LiBF_4$, $LiClO_4$, LiCl, LiBr, LiI, $LiB_{10}Cl_{10}$, $LiCF_3SO_3$, $LiCF_3CO_2$, $LiAsF_6$, $LiSbF_6$, $LiAlCl_4$, $CH_3SO_3Li$, $CF_3SO_3Li$, $LiN(SO_2C_2F_5)_2$, $Li(CF_3SO_2)_2N$, $LiC_4F_9SO_3$, $LiB(C_6H_5)_4$, $LiB(C_2O_4)_2$, $LiPO_2F_2$, $Li(SO_2F)_2N$, LiFSI, and $(CF_3SO_2)_2NLi$.

The solvent component may suitably include one or more selected from the group consisting of a carbonate-based solvent, an ester-based solvent, an ether-based solvent, and a ketone-based solvent.

A term "carbonate-based solvent" as used herein refers to a solvent component having a structure including one or more carbonate group (e.g., R—O—C(O)—O—R', wherein each R and R' is independently hydrocarbon, e.g., alkyl, cycloalkyl, or aryl), which constitutes more than about 50%, about 55%, about 60%, about 65%, about 70%, about 75%, 80%, about 85%, about 90%, about 95%, or about 99% of the total volume of the solvent.

A term "ester-based solvent" as used herein refers to a solvent component having a structure including one or more ester group (e.g., R—O—C(O)—R', wherein each R and R' is independently hydrocarbon, e.g., alkyl, cycloalkyl, or aryl), which constitutes more than about 50%, about 55%, about 60%, about 65%, about 70%, about 75%, 80%, about 85%, about 90%, about 95%, or about 99% of the total volume of the solvent.

A term "ether-based solvent" as used herein refers to a solvent component having a structure including one or more ether group (e.g., R—O—R', wherein each R and R' is independently hydrocarbon, e.g., alkyl, cycloalkyl, or aryl), which constitutes more than about 50%, about 55%, about 60%, about 65%, about 70%, about 75%, 80%, about 85%, about 90%, about 95%, or about 99% of the total volume of the solvent.

A term "ketone-based solvent" as used herein refers to a solvent component having a structure including one or more ketone group (e.g., R—C(O)—R', wherein each R and R' is independently hydrocarbon, e.g., alkyl, cycloalkyl, or aryl), which constitutes more than about 50%, about 55%, about 60%, about 65%, about 70%, about 75%, 80%, about 85%, about 90%, about 95%, or about 99% of the total volume of the solvent.

In an aspect provided is a lithium secondary including the above-described electrolyte solution.

The lithium secondary battery as described herein may be all-solid-state battery that is a rechargeable secondary battery including an electrolyte in a solid state, e.g., gel or polymer (cured), which may include an ionomer and other electrolytic components for transferring ions between the electrodes of the battery.

In addition, the lithium secondary battery may further include a positive electrode including a positive-electrode active material including Ni, Co, and Mn; a negative electrode including a negative-electrode active material including one or more selected from a carbon (C)-based material or a silicon (Si)-based material; and a separator interposed between the positive electrode and the negative electrode.

The positive electrode may suitably include the Ni content of about 60% by weight or greater based on the total weight of the positive electrode.

The negative-electrode active material may suitably include graphite.

The lithium secondary battery may suitably have a capacity retention rate of about 80% or greater after 100 cycles of charging and discharging by performing one cycle of charging and discharging under a condition of 2.5 to 4.2V @ 1 C, 45° C.

The lithium secondary battery may suitably have a capacity retention rate of about 70% or greater after 200 cycles of charging and discharging by performing one cycle of charging and discharging under a condition of 2.5 to 4.2V @ 1 C, 45° C.

Further provided is a vehicle including the above-described lithium secondary battery.

According to various exemplary embodiments of the present disclosure, by the electrolyte solution, a film having high flexibility may be formed on the surface of the positive electrode and a LiF-based solid electrolyte interphase (SEI) may be formed on the surface of the negative electrode to give rigidity to the film having high flexibility, so that cell performance can be improved.

In addition, the insertion and deintercalation process of lithium ion can be smoothly performed by the LiF-based SEI formed on the surface of the negative electrode, thereby improving the output characteristics of a battery.

The term solution as used herein without further limitation may include a variety of fluid compositions, including a single fluid composition or admixtures of two or more fluid materials that may form a true solution or other admixtures such as a dispersion.

Other aspects of the invention are disclosed infra.

DETAILED DESCRIPTION OF THE INVENTION

Figure 1:
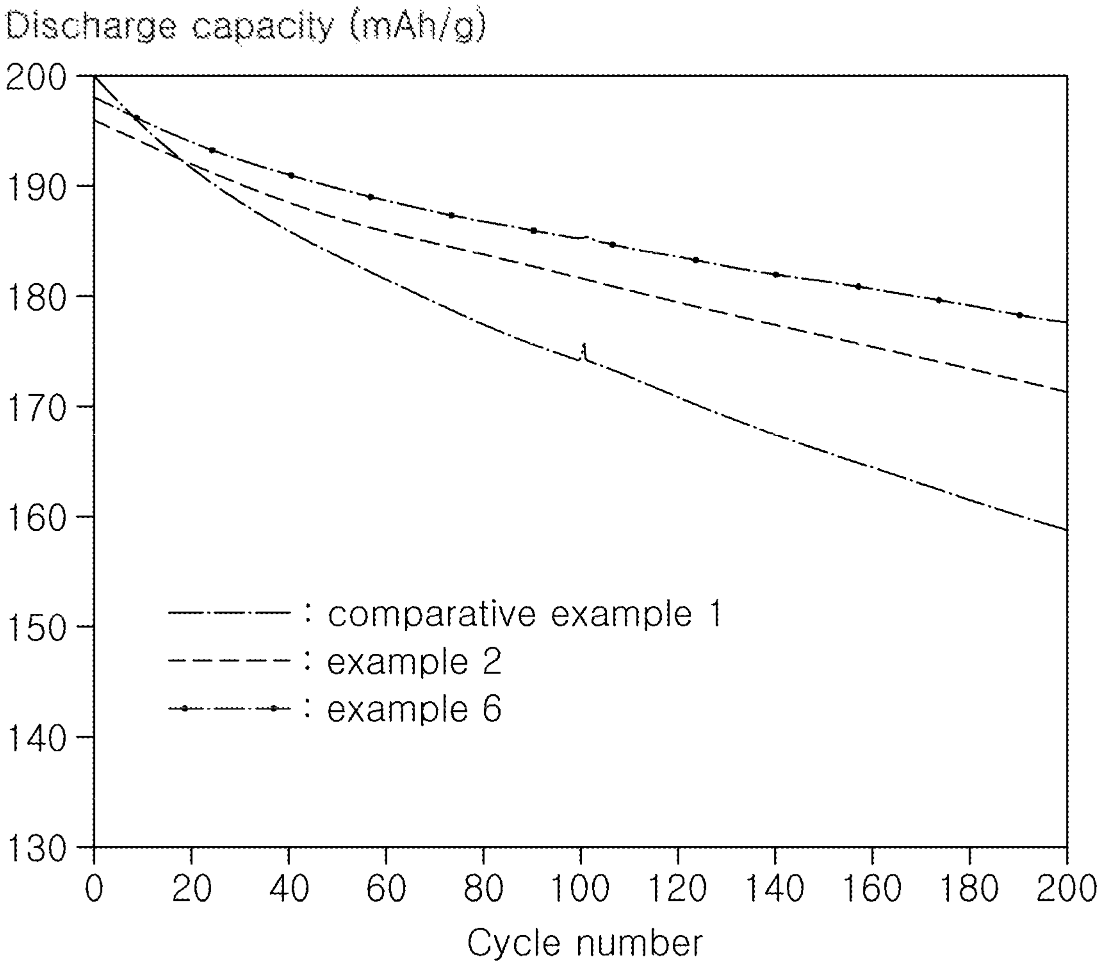
FIGS. 1 and 2 are graphs showing results of experiments for evaluating the lifespan at high temperature for each composition of an electrolyte solution according to Examples and Comparative Examples.

Hereinafter, the embodiments disclosed in the present specification will be described in detail with reference to the accompanying drawings, and the same or similar elements are denoted by the same reference numerals even though they are depicted in different drawings and redundant descriptions thereof will be omitted.

In the following description of the embodiments disclosed in the present specification, a detailed description of known functions and configurations incorporated herein will be omitted when it may make the subject matter of the embodiments disclosed in the present specification rather unclear. In addition, the accompanying drawings are provided only for a better understanding of the embodiments disclosed in the present specification and are not intended to limit technical ideas disclosed in the present specification. Therefore, it should be understood that the accompanying drawings include all modifications, equivalents and substitutions within the scope and sprit of the present disclosure.

It will be understood that although the terms first, second, etc., may be used herein to describe various components, these components should not be limited by these terms. These terms are only used to distinguish one component from another component.

The singular form is intended to include the plural forms as well, unless context clearly indicates otherwise.

In the present application, it will be further understood that the terms "comprises," "includes," etc. specify the presence of stated features, integers, steps, operations, elements, components, or combinations thereof, but do not preclude the presence or addition of one or more other features, integers, steps, operations, elements, components, or combinations thereof.

Unless otherwise indicated, all numbers, values, and/or expressions referring to quantities of ingredients, reaction conditions, polymer compositions, and formulations used herein are to be understood as modified in all instances by the term "about" as such numbers are inherently approximations that are reflective of, among other things, the various uncertainties of measurement encountered in obtaining such values.

Further, unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

In the present specification, when a range is described for a variable, it will be understood that the variable includes all values including the end points described within the stated range. For example, the range of "5 to 10" will be understood to include any subranges, such as 6 to 10, 7 to 10, 6 to 9, 7 to 9, and the like, as well as individual values of 5, 6, 7, 8, 9 and 10, and will also be understood to include any value between valid integers within the stated range, such as 5.5, 6.5, 7.5, 5.5 to 8.5, 6.5 to 9, and the like. Also, for example, the range of "10% to 30%" will be understood to include subranges, such as 10% to 15%, 12% to 18%, 20% to 30%, etc., as well as all integers including values of 10%, 11%, 12%, 13% and the like up to 30%, and will also be understood to include any value between valid integers within the stated range, such as 10.5%, 15.5%, 25.5%, and the like.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

In an aspect, provided is an electrolyte solution for a lithium secondary battery. The electrolyte solution may include a material forming an electrolyte applicable to a lithium secondary battery and may include a lithium salt, a solvent component, and a functional additive.

The lithium salt may suitably include one or more selected from the group consisting of $LiPF_6$, $LiBF_4$, $LiClO_4$, LiCl, LiBr, LiI, $LiB_{10}Cl_{10}$, $LiCF_3SO_3$, $LiCF_3CO_2$, $LiAsF_6$, $LiSbF_6$, $LiAlCl_4$, $CH_3SO_3Li$, $CF_3SO_3Li$, $LiN(SO_2C_2F_5)_2$, $Li(CF_3SO_2)_2N$, $LiC_4F_9SO_3$, $LiB(C_6H_5)_4$, $LiB(C_2O_4)_2$, $LiPO_2F_2$, $Li(SO_2F)_2N$, LiFSI, and $(CF_3SO_2)_2NLi$.

Preferably, the lithium salt may be present at a concentration of about 0.1 to 3.0 moles, preferably about 0.1 to 1.2 moles, in the electrolyte solution.

Also, the solvent component may suitably include one or more selected from the group consisting of a carbonate-based solvent, an ester-based solvent, an ether-based solvent, and a ketone based solvent.

The carbonate-based solvent may suitably include dimethyl carbonate (DMC), diethyl carbonate (DEC), dipropyl carbonate (DPC), methyl propyl carbonate (MPC), ethyl propyl carbonate (EPC), ethyl methyl carbonate (EMC), ethylene carbonate (EC), propylene carbonate (PC), butylene carbonate (BC), fluoroethylene carbonate (FEC), vinylene carbonate (VC), or the like. In addition, the ester-based solvent may be 7-butyrolactone (GBL), n-methyl acetate, n-ethyl acetate, n-propyl acetate, or the like. In addition, the ether-based solvent may be dibutyl ether, or the like, but is not limited thereto.

In addition, the solvent may further include an aromatic hydrocarbon-based organic solvent. Specific examples of the aromatic hydrocarbon-based organic solvent may include benzene, fluorobenzene, bromobenzene, chlorobenzene, cyclohexylbenzene, isopropylbenzene, n-butylbenzene, octylbenzene, toluene, xylene, mesitylene, and the like, and this solvent may be used alone or in combination.

Meanwhile, a first electrode film additive may include (4-(1H-1,2,4-triazol-1-yl)phenyl)(fluorosulfonyl)sulfamoyl fluoride (hereinafter referred to as "HN-003"), represented by the following [Formula 1], may be used as the functional additive added to an electrolyte solution.

[Formula 1]

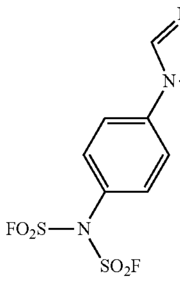

The first electrode film additive may preferably be (4-(1H-1,2,4-triazol-1-yl)phenyl)(fluorosulfonyl)sulfamoyl fluoride(HN-003), which may form a film having high flexibility on the surface of the positive electrode and form a LiF-based solid electrolyte interphase (SEI) on the surface of the negative electrode.

In particular, the first electrode film additive may have a relatively low HOMO and LUMO energy levels when comparing HOMO and LUMO energy levels through DFT calculation, and is first decomposed at the negative electrode to form an SEI layer.

Also, an N-derived layer may be formed on the positive electrode and the negative electrode by the 1,2,4-triazole group of the first electrode film additive, thereby contributing to the improvement of cycle stability and cell lifespan.

The first electrode film additive may include a (fluorosulfonyl)imide structure to form a stable and uniform SEI layer and linear decomposition through a high degree of reduction like LiFSI.

The first electrode film additive, e.g., (4-(1H-1,2,4-triazol-1-yl)phenyl)(fluorosulfonyl)sulfamoyl fluoride(HN-003), may be preferably added in an amount of about 0.01 to 0.5% by weight based on the total weight of the electrolyte solution. Preferably, the first electrode film additive may be added in an amount of about 0.01 to 0.3% by weight based on the total weight of the electrolyte solution. More preferably, the first electrode film additive is preferably added in an amount of about 0.1 to 0.3% by weight based on the total weight of the electrolyte solution.

When the amount of the first electrode film additive to be added is less than the above presented range, e.g., less than about 0.01% by weight, it is difficult to form a sufficient surface protective film on the surface of the positive and negative electrodes and thus a sufficient effect cannot be expected, and when the amount of the first electrode film additive is greater than the above presented range, e.g., greater than about 0.5% by weight, the surface protective layer, SEI, may be excessively formed and the cell resistance increases, and thus the lifespan of the cell may be deteriorated.

Meanwhile, as the functional additive, a negative-electrode film additive, serving to form a surface protective film on the negative electrode may be further added together with the first electrode film additive. For example, the negative-electrode film additive may be a vinylene carbonate (hereinafter referred to as "VC").

In this case, the VC used as the negative-electrode film additive may be preferably added in an amount of about 0.5 to 2.0% by weight based on the total weight of the electrolyte solution. More preferably, the negative-electrode film additive may be added in an amount of about 1.0% by weight based on the total weight of the electrolyte solution.

When the amount of the negative-electrode film additive to be added is less than the above presented amount, e.g., less than about 0.5% by weight, there is a problem in that the long-term lifespan of the cell is deteriorated, and when the amount of the negative-electrode film additive is greater than the above presented amount, e.g., greater than about 2.0% by weight, there are problems in that the cell resistance may increase due to the excessive formation of the surface protective layer, resulting in reduced battery output.

As the functional additive, a second electrode film additive may form a surface protective film on the positive and negative electrodes may be further added together with the first electrode film additive and the negative-electrode film additive. For example, lithium difluorophosphate (hereinafter, referred to as "$LiPO_2F_2$") may be used as the electrode film additive.

Preferably, $LiPO_2F_2$ used as the second electrode film additive may be added in an amount of about 0.5 to 2.0% by weight based on the total weight of the electrolyte solution. More preferably, the second electrode film additive may be added in an amount of about 1.0% by weight based on the total weight of the electrolyte solution.

When the amount of the second electrode film additive to be added is less than the above presented amount, e.g., less than about 0.5% by weight, there is a problem in that the long-term lifespan of the cell is deteriorated, and when the amount of the second electrode film additive is greater than the above presented amount, e.g., greater than about 2.0% by weight, there are problems in that the cell resistance may increase due to the excessive formation of the surface protective layer, resulting in reduced battery output.

In an aspect, provided is a lithium secondary battery including a positive electrode, a negative electrode, and a separator, in addition to the above-described electrolyte solution.

The positive electrode may suitably include an NCM-based positive-electrode active material containing Ni, Co, and Mn. In particular, the positive-electrode active material included in the positive electrode in this embodiment preferably contains an NCM-based positive-electrode active material including the Ni content in an amount of about 60% by weight or greater based on the total weight of the positive electrode.

The negative electrode includes one or more selected from a carbon (C)-based negative-electrode active material and a silicon (Si)-based negative-electrode active material.

The carbon (C)-based negative-electrode active material may include at least one material selected from the group consisting of artificial graphite, natural graphite, graphitized carbon fiber, graphitized mesocarbon microbeads, fullerene, and amorphous carbon. Preferably, artificial graphite or natural graphite may be used as the negative-electrode active material.

In addition, the silicon (Si)-based negative active material includes silicon oxide, silicon particles, and silicon alloy particles.

The positive electrode and the negative electrode may be produced by mixing each of active materials with a conductive material, a binder, and a solvent to prepare an electrode slurry, and then directly coating a current collector with the electrode slurry, followed by drying. For example, aluminum (Al) may be used as the current collector, but the present disclosure is not limited thereto. Since such an electrode production method is well known in the art, a detailed description thereof will be omitted.

The binder serves to promote adhesion between particles of each active material or adhesion thereof to the current collector. For example, the binder may be polyvinyl alcohol, carboxymethyl cellulose, hydroxypropyl cellulose, diacetyl cellulose, polyvinyl chloride, carboxylated polyvinylchloride, polyvinylfluoride, an ethylene-oxide-containing polymer, polyvinylpyrrolidone, polyurethane, polytetrafluoroethylene, polyvinylidene fluoride, polyethylene, polypropylene, styrene butadiene rubber, acrylated styrene butadiene rubber, an epoxy resin, nylon, or the like, but is not limited thereto.

In addition, the conductive material may impart conductivity to the electrode, and any conductive material can be used, as long as it is an electrically conductive material that does not cause a chemical change in the battery to be produced, and examples thereof include natural graphite, artificial graphite, carbon black, acetylene black, Ketjen black, carbon fibers, metal powders such as copper, nickel, aluminum and silver powders, metal fibers, and the like. In addition, a conductive material such as a polyphenylene derivative may be used alone or in combination.

The separator inhibits a short circuit between the positive electrode and the negative electrode, and provides a passage for lithium ions. Such a separator may be a well-known separator, for example, polyolefin-based polymer membranes such as polypropylene, polyethylene, polyethylene/polypropylene, polyethylene/polypropylene/polyethylene, and polypropylene/polyethylene/polypropylene, or multiple membranes, microporous films, woven fabrics and nonwoven fabrics thereof. In addition, a porous polyolefin film coated with a resin having excellent stability may be used as the separator.

EXAMPLE

Hereinafter, the present disclosure will be described with reference to Examples and Comparative Examples according to the present disclosure.

<Experiment 1> Experiment on Capacity Retention Rate at High Temperature (45° C.) According to the Type and Amount of Functional Additive In order to determine a capacity retention rate at high temperature depending on the type and amount of a functional additive added to the electrolyte solution, a capacity retention rate characteristic at high temperature of 45° C. after 100 cycles and 200 cycles of charging and discharging was measured while the type and amount of the functional additive were changed as shown in the following Table 1, and the results were shown in Table 1 and in FIGS. 1 and 2.

In this case, the experiment was carried out under the following conditions: a cut-off voltage of 2.5 to 4.2 V a C-rate of 1 C, and temperature of 45° C. The lithium salt used to prepare the electrolyte solution was 1M $LiPF_6$, and the solvent used was a solvent mixture containing ethylene carbonate (EC), ethyl methyl carbonate (EMC) and diethyl carbonate (DEC) at a volume ratio of 25:45:30.

Also, the experiment was conducted under full cell condition using the mixture of NCM811 and NCM622 as the positive electrode, and graphite as the negative electrode.

TABLE 1

| | Additive (wt %) | | | Lifespan capacity retention rate (%) | |
|---|---|---|---|---|---|
| Category | HN-003 | $LiPO_2F_2$ | VC | @ 100 cyc | @200 cyc |
| Comparative Example 1 | — | — | — | 86.9 | 79.2 |
| Comparative Example 2 | — | — | 1.0 | 90.8 | 85.1 |
| Comparative Example 3 | — | 1.0 | 1.0 | 91.8 | 86.6 |
| Example 1 | 0.01 | — | 1.0 | 81.0 | 72.5 |
| Example 2 | 0.1 | — | 1.0 | 92.8 | 87.5 |
| Example 3 | 0.3 | — | 1.0 | 87.8 | 80.4 |
| Example 4 | 0.5 | — | 1.0 | 89.6 | 82.8 |
| Example 5 | 0.1 | — | — | 87.0 | 77.8 |
| Example 6 | 0.1 | 1.0 | 1.0 | 93.5 | 89.6 |

Figure 2:
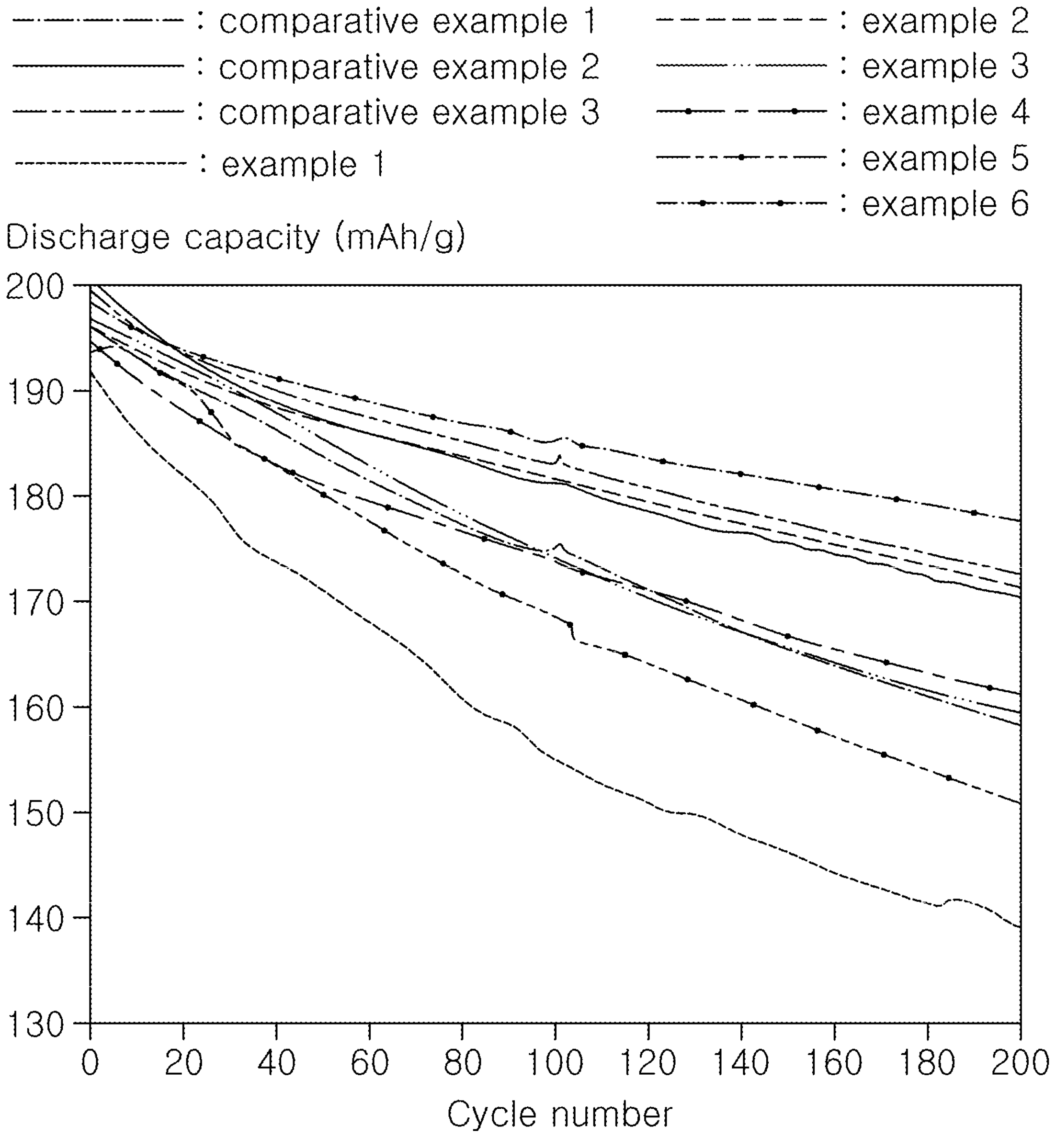

As shown in Table 1 and FIGS. 1 and 2, Example 5, in which HN-003, which was the first electrode film additive, was added alone as the functional additive, exhibited a level of lifespan capacity retention rate at high temperature similar to that of Comparative Example 1 in which no functional additive was added.

In addition, Examples 2 to 4 in which VC, the negative-electrode film additive, was added together with the first electrode film additive as the functional additive, improved lifespan capacity retention rate at high temperature, compared to Comparative Example 1 in which no functional additive was added.

In particular, Example 2, in which 0.1% by weight of VC and 1.0% by weight of the negative-electrode film additive were respectively added together with the first electrode film additive as the functional additive, lifespan capacity retention rate at high temperature was significantly improved compared to Comparative Example 1. Also, Example 2 significantly improved capacity retention rate at high temperature compared to Comparative Example 2 in which VC was added alone as the negative-electrode film additive, without adding the first electrode film additive, and Comparative Example 3, in which the negative-electrode film additive of VC and the second electrode film additive of $LiPO_2F_2$ were added.

Also, Example 6, in which $LiPO_2F_2$, the second electrode film additive, was added along with the first electrode film additive and the negative-electrode film additive as the functional additive, significantly improved lifespan capacity retention rate at high temperature compared to Comparative Examples 1 to 3, and that Example 6 also significantly improved lifespan capacity retention rate at high temperature compared to other Examples.

Accordingly, when HN-003, the first electrode film additive, was added alone as the functional additive, or when the negative-electrode film additive of VC and the second electrode film additive of $LiPO_2F_2$ were added together with the first electrode film additive as the functional additive, the capacity retention rate was maintained at 80% or greater after 100 cycles of charging and discharging, and at 70% or greater even after 200 cycles of charging and discharging.

In addition, when the negative-electrode film additive of VC and the second electrode film additive of $LiPO_2F_2$ were added together with the first electrode film additive within the amount ranges presented in the disclosure, the capacity retention rate was maintained at 90% or greater after 100 cycles of charging and discharging and at 80% or greater even after 200 cycles of charging and discharging.

<Experiment 2> Experiment on Output Performance at Room Temperature (25° C.) According to the Type and Amount of Functional Additive In order to determine the output performance characteristics at room temperature depending on the type and amount of functional additive added to the electrolyte solution, the output performance at room temperature of 25° C. was measured while the type and amount of the functional additive were changed as shown in the following Table 2, and the results were shown in Table 2 and in FIG. 3.

In this case, the experiment was carried out under the following conditions: a cut-off voltage of 2.5 to 4.2 V a C-rate: charged at 0.5 C, 1.0 C, 2.0 C, 3.0 C/discharged at 0.5 C, and a temperature of 25° C. The lithium salts used to prepare the electrolyte solution were 0.5 M $LiPF_6$ and 0.5M LiFSI, and the solvent used was a solvent mixture containing ethylene carbonate (EC), ethyl methyl carbonate (EMC) and diethyl carbonate (DEC) at a volume ratio of 25:45:30.

Also, the experiment was conducted under full cell condition using the mixture of NCM811 and NCM622 as the positive electrode, and graphite as the negative electrode.

TABLE 2

| | Additive (wt %) | | | Output performance (%) | | |
|---|---|---|---|---|---|---|
| Category | HN-003 | $LiPO_2F_2$ | VC | @ 1 C | @2 C | @3 C |
| Comparative Example 1 | — | — | — | 96.3 | 86.8 | 75.6 |
| Comparative Example 2 | — | — | 1.0 | 96.6 | 84.9 | 72.9 |
| Comparative Example 3 | — | 1.0 | 1.0 | 95.6 | 86.0 | 76.3 |
| Example 1 | 0.01 | — | 1.0 | 95.9 | 87.5 | 78.7 |
| Example 2 | 0.1 | — | 1.0 | 95.8 | 87.6 | 78.7 |
| Example 3 | 0.3 | — | 1.0 | 95.4 | 85.4 | 74.0 |
| Example 4 | 0.5 | — | 1.0 | 95.1 | 79.7 | 68.7 |
| Example 5 | 0.1 | — | — | 96.2 | 86.4 | 75.0 |
| Example 6 | 0.1 | 1.0 | 1.0 | 95.4 | 87.6 | 79.1 |

Figure 3:
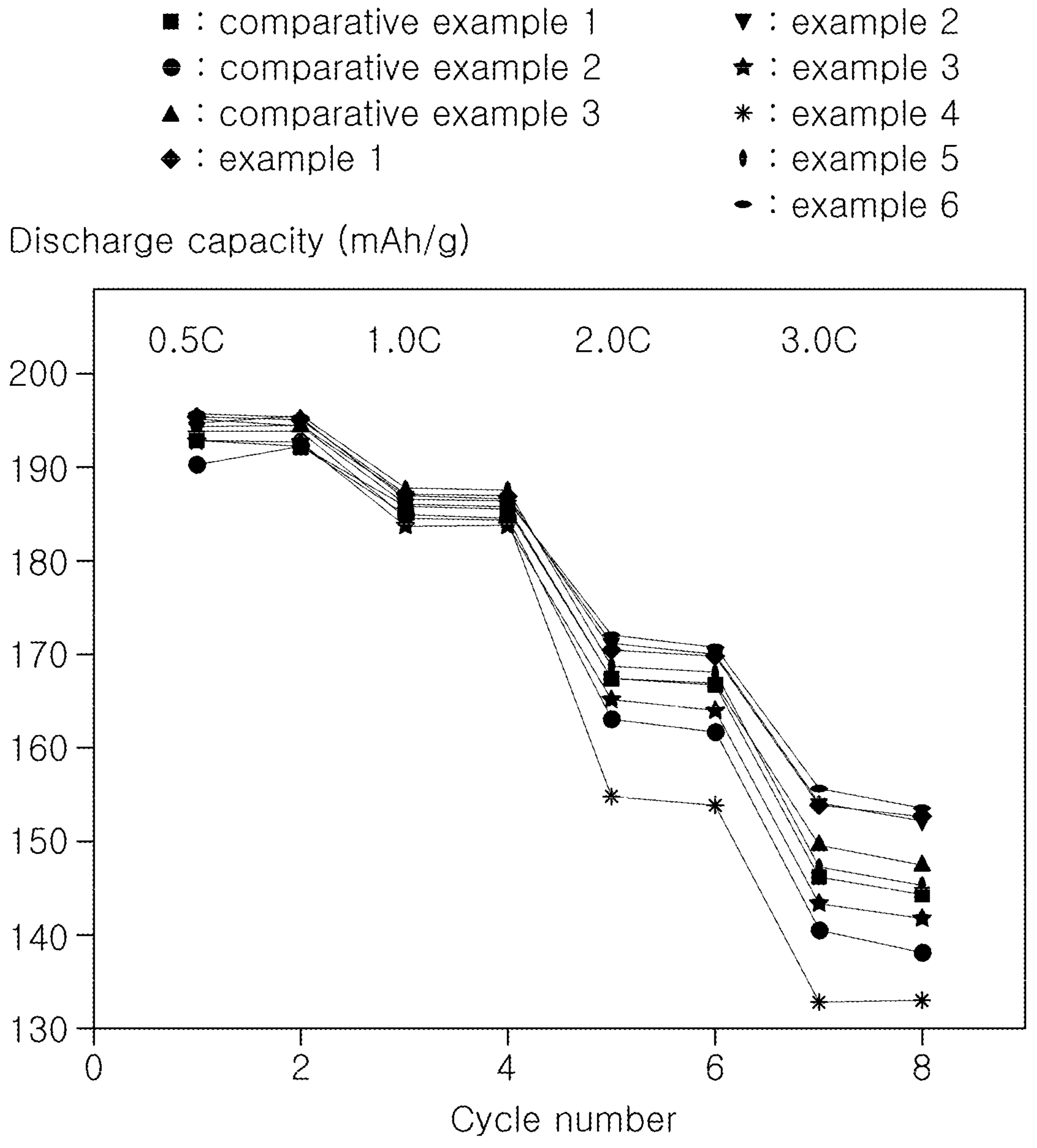
FIG. 3 is a graph showing results of experiments for evaluating output characteristics at room temperature for each composition of an electrolyte solution according to Examples and Comparative Examples.

As shown in Table 2 and FIG. 3, Example 5, in which HN-003 was added alone as the functional additive and the first electrode film additive, overall improved output performance at room temperature compared with Comparative Example 1 in which no functional additive was added.

In addition, Examples 2 to 4, in which the negative-electrode film additive of VC was added together with the first electrode film additive as the functional additive, exhibited similar output performance or partially improved output performance at room temperature compared to Comparative Example 1 in which no functional additive was added.

In particular, Example 2, in which 0.1% by weight and 1.0% by weight of VC as the negative-electrode film additive, were respectively added together with the first electrode film additive as the functional additive, overall improved output performance at room temperature compared to Comparative Example 1. Also, Example 2 overall improved output performance at room temperature compared to Comparative Example 2 in which the negative-electrode film additive of VC was added alone without adding the first electrode film additive, and Comparative Example 3 in which the negative-electrode film additive of VC and the second electrode film additive of $LiPO_2F_2$ were added.

In addition, Example 6, in which the second electrode film additive of $LiPO_2F_2$ was added together with the first electrode film additive and the negative-electrode film additive, significantly improved the output performance at room temperature compared to Comparative Examples 1 to 3 and that Example 6 significantly improved output performance at room temperature compared to other Example.

Therefore, as shown from the above experiments, HN-003, which was the first electrode film additive, was preferably added in an amount of 0.01 to 0.5% by weight, preferably 0.01 to 0.3% by weight, more preferably 0.1 to 0.3% by weight, based on the weight of the electrolyte solution, in terms of high temperature lifespan characteristics and room temperature output characteristics.

In particular, according to various exemplary embodiments of the present disclosure above, high temperature lifespan characteristics and the room temperature output characteristics can be significantly improved when VC, the negative-electrode film additive, and $LiPO_2F_2$, the second electrode film additive, may be added together with HN-003, the first electrode film additive, as the functional additive.

Although the present disclosure has been described with reference to the accompanying drawings and the above-described exemplary embodiments, the present disclosure is not limited thereto, and is defined by the claims described below. Therefore, those skilled in the art will appreciate that various modifications, additions and substitutions are possible, without departing from the scope and spirit of the present disclosure.

What is claimed is:

1. An electrolyte solution for a lithium secondary battery, comprising:

a lithium salt;

a solvent component; and a functional additive, wherein the functional additive comprises (4-(1H-1,2,4-triazol-1-yl)phenyl)(fluorosulfonyl)sulfamoyl fluoride, represented by the following Formula 1.

[Formula 1]

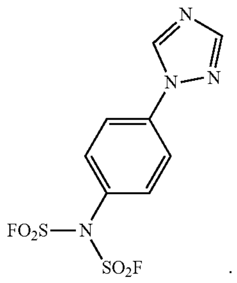

2. The electrolyte solution of claim 1, wherein the electrolyte solution comprises the (4-(1H-1,2,4-triazol-1-yl) henyl) (fluorosulfonyl) sulfamoyl fluoride in an amount of about 0.01 to 0.5% by weight based on the total weight of the electrolyte solution.

3. The electrolyte solution of claim 2, wherein the electrolyte solution comprises the (4-(1H-1,2,4-triazol-1-yl)phenyl) (fluorosulfonyl) sulfamoyl fluoride in an amount of about 0.01 to 0.3% by weight based on the total weight of the electrolyte solution.

4. The electrolyte solution of claim 1, wherein the functional additive further comprises vinylene carbonate (VC).

5. The electrolyte solution of claim 4, wherein the electrolyte solution comprises the vinylene carbonate (VC) in an amount of about 0.5 to 2.0% by weight based on the total weight of the electrolyte solution.

6. The electrolyte solution of claim 4, wherein the functional additive further comprises lithium difluorophosphate ($LiPO_2F_2$).

7. The electrolyte solution of claim 6, wherein the electrolyte solution comprises the lithium difluorophosphate ($LiPO_2F_2$) in an amount of about 0.5 to 2.0% by weight based on the total weight of the electrolyte solution.

8. The electrolyte solution of claim 1, wherein the lithium salt comprises one or more selected from the group consisting of $LiPF_6$, $LiBF_4$, $LiClO_4$, LiCl, LiBr, LiI, $LiB_{10}Cl_{10}$, $LiCF_3SO_3$, $LiCF_3CO_2$, $LiAsF_6$, $LiSbF_6$, $LiAlCl_4$, $CH_3SO_3Li$, $CF_3SO_3Li$, LiN $SO_2C_2F_5)_2$, $Li(CF_3SO_2)_2N$, $LiC_4F_9SO_3$, $LiB(C_6H_5)_4$, $LiB(C_2O_4)_2$, $LiPO_2F_2$, $Li(SO_2F)_2N$, LiFSI, and $(CF_3SO_2)_2NLi$.

9. The electrolyte solution of claim 1, wherein the solvent includes one or a mixture of two or more selected from the group consisting of a carbonate-based solvent, an ester-based solvent, an ether-based solvent, and a ketone-based solvent.

10. A lithium secondary battery comprising the electrolyte solution of claim 1.

11. The lithium secondary battery of claim 10, further comprising:

a positive electrode comprising a positive-electrode active material comprising Ni, Co, and Mn;

a negative electrode comprising a negative-electrode active material comprising one or more selected from a carbon (C)-based material or a silicon (Si)-based material; and a separator interposed between the positive electrode and the negative electrode.

12. The lithium secondary battery of claim 11, wherein the positive electrode comprises the Ni content of about 60% by weight or greater based on the total weight of the positive electrode.

13. The lithium secondary battery of claim 11, wherein the negative-electrode active material comprises graphite.

14. The lithium secondary battery of claim 10, wherein the lithium secondary battery has a capacity retention rate of about 80% or greater after 100 cycles of charging and discharging by performing one cycle of charging and discharging under a condition of 2.5 to 4.2V @ 1C, 45°C.

15. The lithium secondary battery of claim 10, wherein the lithium secondary battery has a capacity retention rate of about 70% or greater after 200 cycles of charging and discharging by performing one cycle of charging and discharging under a condition of 2.5 to 4.2V @ 1C, 45°C.

16. A vehicle comprising a lithium secondary battery of claim 10.

17. An electrolyte composition for a lithium secondary battery, comprising:

a lithium salt; and (4-(1H-1,2,4-triazol-1-yl)phenyl)(fluorosulfonyl)sulfamoyl fluoride, represented by the following Formula 1.

[Formula 1]

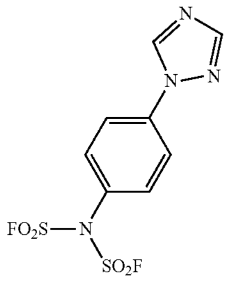

.

* * * * *